(12) United States Patent
Miyashita et al.

(10) Patent No.: US 6,567,115 B1
(45) Date of Patent: May 20, 2003

(54) SOLID-STATE IMAGING DEVICE (75) Inventors: Taketo Miyashita, Tokyo (JP); Hitoshi Kajinami, Tokyo (JP); Yasuyuki Suzuki, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 09/473,656

(22) Filed: Dec. 29, 1999

(30) Foreign Application Priority Data

Jan. 7, 1999 (JP) .......................................... 11-002094

(51) Int. Cl.⁷ ................................................ H04N 9/47
(52) U.S. Cl. ...................................................... 348/76
(58) Field of Search ............................ 348/65, 75, 76, 348/294, 72; 257/680, 723, 290, 291; 357/80, 75, 74; 438/66, 75, 977; 600/109, 112, 130; H04N 9/47

(56) References Cited

U.S. PATENT DOCUMENTS

| | | | | |
|---|---|---|---|---|
| 4,786,965 A | * | 11/1988 | Yabe .......................... 348/76 |
| 4,831,456 A | * | 5/1989 | Takamura .................. 348/374 |
| 4,868,644 A | * | 9/1989 | Yabe et al. ................. 348/76 |
| 4,918,521 A | * | 4/1990 | Yabe et al. ................. 348/76 |
| 5,220,198 A | * | 6/1993 | Tsuji .......................... 257/731 |

* cited by examiner

Primary Examiner—Vu Le
Assistant Examiner—Behrooz Senfi
(74) Attorney, Agent, or Firm—Sonnenschein, Nath & Rosenthal (57) ABSTRACT

The object of the present invention is to provide a solid-state imaging device making it possible to downsize an imaging unit and further decrease the diameter of the front end of an electronic endoscope. A bonding pad (25) provided in the outer periphery of a solid-state imaging chip (18) and a bonding pad (26) provided in a vertical substrate (20a) combined with the back of the solid-state imaging chip (18) are connected with each other by connection means (29) constituted of a film with a wiring pattern formed, a horizontal substrate (20b) is combined with the back of the substrate (20a), electronic components (19) are mounted on the stepped surface of the substrate (20b) retreating from the substrate (20a) and a signal cable (30) is connected to a terminal portion (27) formed at an end of the stepped surface of the substrate (20b) so that the substrates (20a) and (20b) and electronic components (19) mounted on the substrate (20b), and terminal portion (27) of the signal cable are set in the projection area of the solid-state imaging chip (18).

5 Claims, 7 Drawing Sheets

SOLID-STATE IMAGING DEVICE

RELATED APPLICATION DATA

The present application claims priority to Japanese Application No. P11-002094 filed Jan. 7, 1999, which application is incorporated herein by reference to the extent permitted by law.

BACKGROUND OF THE INVENTION

1. Technical Field

The present invention relates to a solid-state imaging device to be applied to an electronic endoscope or the like, particularly to a solid-state imaging device constituted so that a circuit board and electronic components mounted on the circuit board can be set in the projection area of a not-packaged solid-state imaging chip including a CCD and thereby, a solid-state imaging unit can be downsized and thus, the outside diameter of the front end of the electronic endoscope can be decreased.

2. Description of the Related Art

In recent years, various types of electronic endoscopes respectively using a solid-state imaging chip such as a charge-coupled device (CCD) as an imaging means and the like are proposed, of which the solid-state imaging chip is embedded in the front end of a tube inserted into the body of an endoscope. Therefore, a thinner and shorter tube front end is preferable in order to ease the pain of a patient. However, in order to decrease the tube in diameter and length, how the solid-state imaging chip can be downsized has been an important technical problem.

Figure 1:
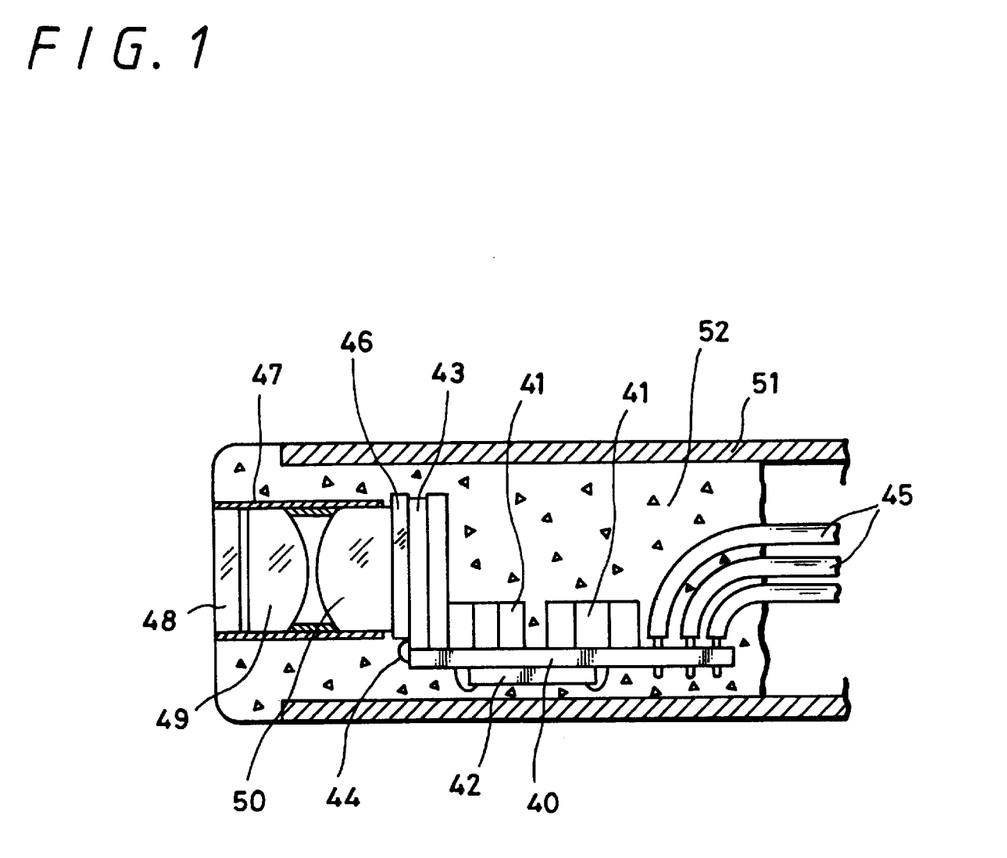
FIG. 1 is a sectional view of an endoscope containing a conventional solid-state imaging device.

A conventional endoscope using a solid-state imaging chip is disclosed in U.S. Pat. No. 2,607,542 (Japanese Patent Laid-Open No. 313970/1988). FIG. 1 shows a composition of one example of the endoscope. Electronic components 41 and 42 are mounted on one plane (upper plane) and the other plane (lower plane) of a horizontally-set circuit board shown by symbol 40. A not-packaged solid-state imaging chip 43 is perpendicularly combined with one plane of the front end of the circuit board 40 separately from the electronic component 41. Moreover, an end of the circuit board 40 and a not-illustrated bonding pad provided in the front surface of the solid-state imaging chip 43 are electrically connected with each other by a bonding wire 44. Furthermore, a signal cable 45 is connected to the rear end of the circuit board 40.

Meanwhile, the front surface of the solid-state imaging chip 43 is airtightly covered with a cover glass 46 and optical lenses 48, 49, and 50 supported by a lens barrel 47 are arranged in front of the cover glass 46 so as to oppose the optical axis of the solid-state imaging chip 43. Moreover, the above-mentioned respective components are covered with a sheath 51 and the space in the sheath 51 is filled with a molding material 52.

With the endoscope constituted as mentioned above, however, because the end surface of the circuit board 40 is connected with the solid-state imaging chip 43 by the bonding wire 44, a space for bonding is required in the outside-diameter direction of the solid-state imaging chip 43. Therefore, it cannot be avoided that the outside diameter of the front end of the endoscope increases by a value equivalent to the size of the space and this prevents the diameter from decreasing.

SUMMARY OF THE INVENTION

The present invention is implemented to solve the above problems and its object is to provide a solid-state imaging device capable of downsizing an imaging unit and thereby, further decreasing the diameter at the front end of an endoscope.

The present invention provides a solid-state imaging device comprising:
 a not-packaged solid-state imaging chip;
 a circuit board which is combined with the plane on the opposite side of the imaging plane of the solid-state imaging chip and on which electronic components are mounted; and
 a connection means constituted of a film on which a wiring pattern for electrically connecting a bonding pad provided in the outer peripheral portion of the imaging plane of the solid-state imaging chip with a bonding pad provided in the circuit board is formed; wherein
 the electronic components are mounted on the stepped portion of the circuit board formed lower than the outline of said solid-state imaging chip and a signal cable is connected to an end of said stepped portion so that said electronic components mounted on said circuit board and the terminal portion of the cable are arranged in the projection area of said solid-state imaging chip.

Moreover, the present invention provides another solid-state imaging device comprising:
 a not-packaged solid-state imaging chip;
 a circuit board which is combined with the plane on the opposite side of the imaging plane of the solid-state imaging chip and on which electronic components are mounted; and
 a connection means constituted of a bonding wire for electrically connecting a bonding pad provided in the outer peripheral portion of the imaging plane of said solid-state imaging chip with a bonding pad provided in the circuit board; wherein
 said electronic components are mounted on the stepped portion of the circuit board formed lower than the outline of said solid-state imaging chip and a signal cable is connected to an end of said stepped portion so that said electronic components mounted on said circuit board and the terminal portion of the cable are arranged in the projection area of said solid-state imaging chip.

BRIEF DESCRIPTION OF THE DRAWINGS

FIG. 5 is a perspective view of a circuit board with electronic components mounted on;

DETAILED DESCRIPTION OF THE PREFERRED EMBODIMENT

A case is described below in which an embodiment of a solid-state imaging device of the present invention is applied to an electronic endoscope by referring to the accompanying drawings.

Figure 2:
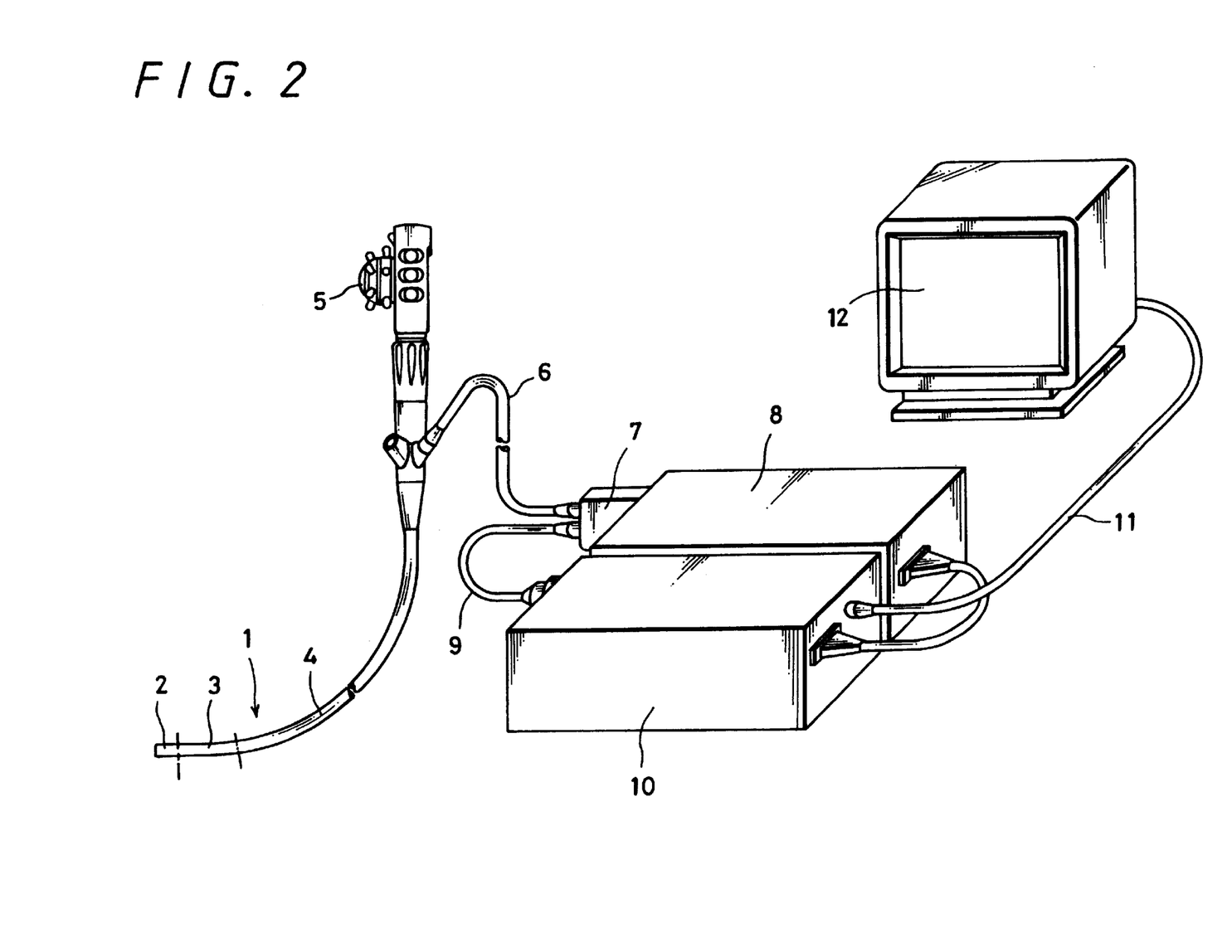
FIG. 2 is a perspective view of the outward appearance of the whole of an electronic endoscope.

FIG. 2 is a perspective view of the outward appearance of an electronic endoscope (hereafter referred to as an endoscope).

An endoscope 1 comprising a tube has a solid-state imaging chip for photographing a portion to be photographed through an object glass at its front end 2 and the electronic endoscope 1 is inserted into a body from the front end 2 to photograph a portion in the body so that a medical treatment can be performed by a treatment tool such as a forceps and the like extending from the endoscope 1.

The front end of the endoscope 1 is a hard portion and the rear side of the front end 2 is provided with a bend portion 3 to be bent by following the change of camera angles and the rear side of the bend portion 3 is provided with a flexible soft portion 4 which can be inserted into a body cavity. The rear end of the soft portion 4 is connected to an operating portion 5 also serving as a holding portion and a universal cord 6 in which a signal cable, light guide fiber, and various fluid conduits are set is connected from the operating portion 5.

The universal cord 6 is connected to a light-source unit 8 through a connector 7 and moreover connected to a video processor 10 from the connector 7 through a cable 9. Furthermore, the cord 6 is connected to a monitor 12 from the video processor 10 through an output cable 11. Therefore, a video signal of a portion photographed by the endoscope 1 is signal-processed by the video processor 10 and displayed by the monitor 12.

Figure 3:
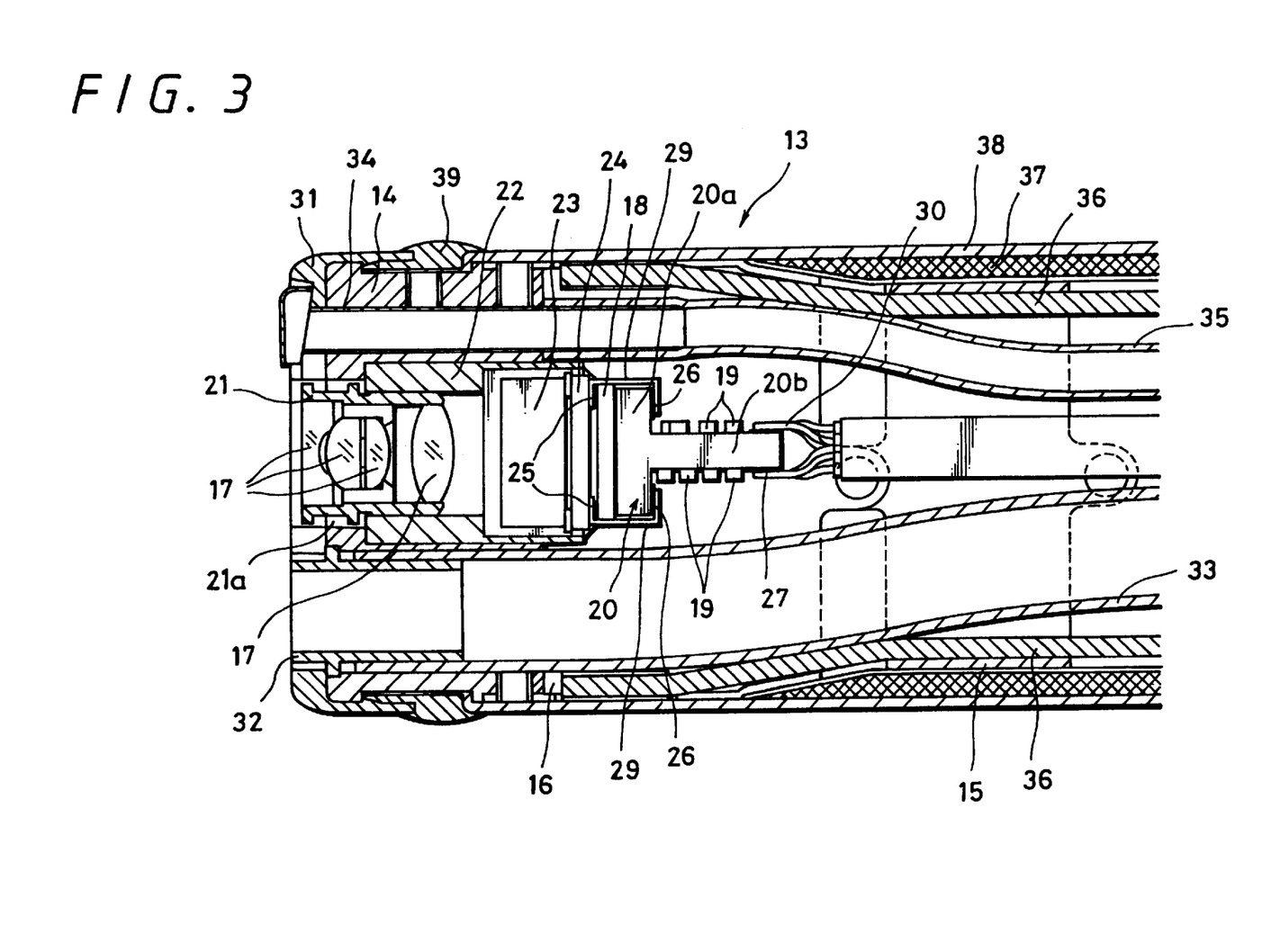
FIG. 3 is an enlarged sectional view of the front end of an endoscope.
Figure 4:
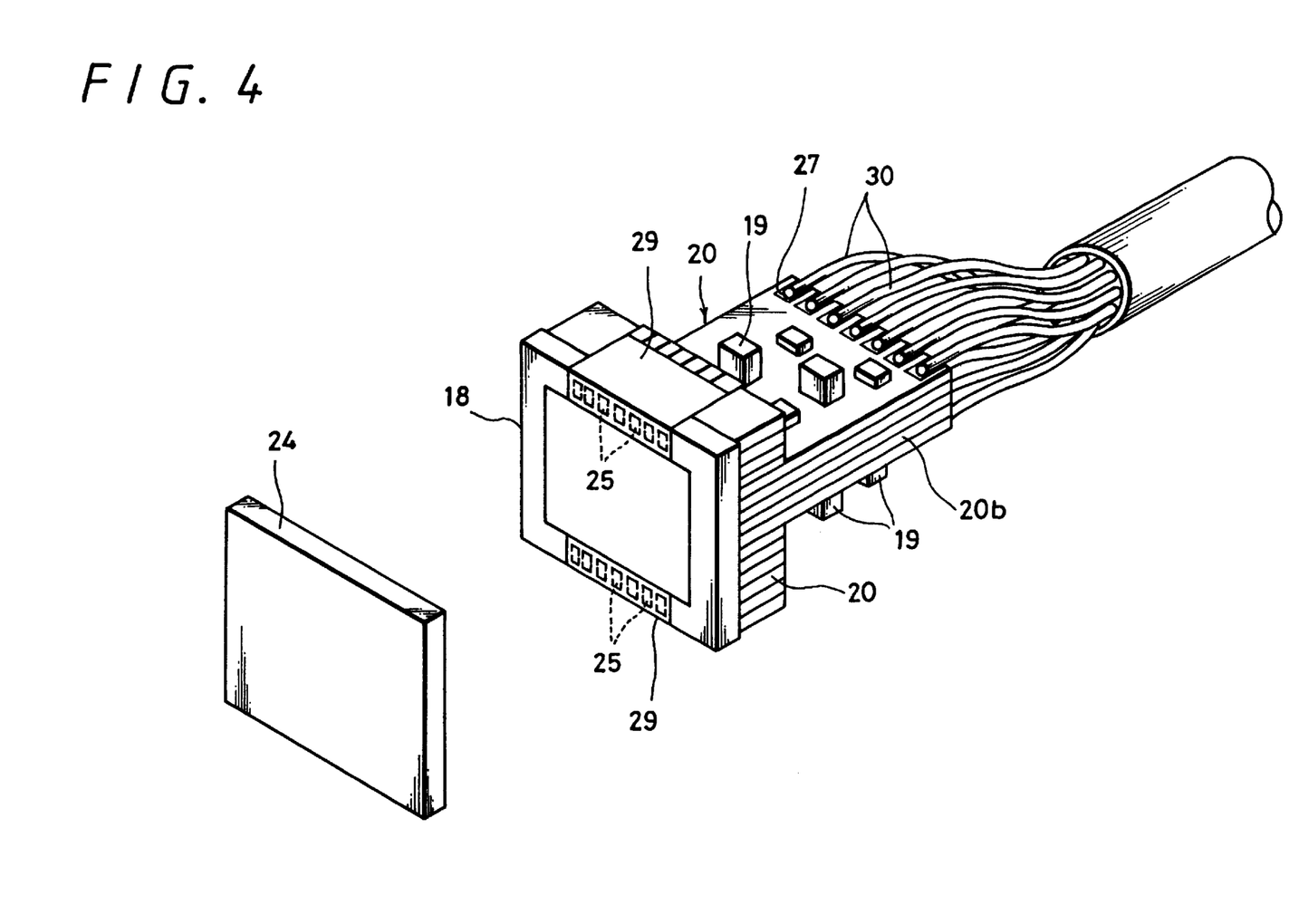
FIG. 4 is a perspective view of a solid-state imaging device of the present invention.

Then, the detailed composition of the imaging unit set to the front end 2 of the endoscope 1 is described below by referring to FIGS. 3 and 4. FIG. 3 is an enlarged longitudinal sectional view of the front end of an endoscope in which a solid-state imaging device is embedded and FIG. 4 is a perspective view of a solid-state imaging device.

Symbol 13 denotes the whole of an imaging unit. The imaging unit 13 uses a cylindrical main body portion 14 made of a metallic hard member as the base in which a tip pipe 16 serving as a fixed end of a joint piece rotatably set by components of the bend portion 3 is fixed to the rear end of the main body portion 14 and an optical lens system 17 comprising a plurality of groups of lenses including an object glass and the like, solid-state imaging chip 18, and a circuit board 20 on which circuit components 19 including capacitors and transistors are mounted are stored in the tip pipe 16.

The optical lens system 17 is held by a lens barrel 21, moreover held by a collar 22 so as to accurately align the optical axis of the optical lens system 17 with the effective pixel center of the solid-state imaging chip 18, and fixed by not-illustrated screws so as it can be disassembled. Moreover, drain or air is prevented from entering a concave portion 21a provided in the outer periphery of the lens barrel 21 by making the range between the portion 21a and the body 14 airtight by an O-ring.

A color filter 23 is set to the rear of the optical lens system 17 in the collar 22 and bonded by an epoxy-based adhesive so that a cover glass 24 set to the back of the color filter 23 does not interrupt these effective pixel areas.

Moreover, the not-packaged above-described solid-state imaging chip 18 is set to the back of the cover glass 24 so that portions to which the optical lens system 17 is projected are superposed each other. The cover glass 24 is sealed by, for example, an epoxy-based adhesive so that dust, drain, or gas does not enter the pixel area of the solid-state imaging chip 18. On the solid-state imaging chip 18, for example, an almost rectangular image area of 4.47 mm by 3.8 mm is formed and a plurality of bonding pads 25 and 25 are formed at upper and lower sides around the image area.

The circuit board 20 is fixed to the back of the solid-state imaging chip 18. The circuit board 20 comprises a so-called T-shaped multilayer ceramic plate constituted of a vertical substrate 20a fixed to the back of solid-state imaging chip 18 and the horizontal substrate 20b set so as to be orthogonal to the substrate 20a. The circuit board 20 is more minutely described below. The vertical substrate 20a has a size that can be kept in the projection area of the solid-state imaging chip 18 and is accurately fixed to the solid-state imaging chip 18 by an epoxy-based adhesive.

Figure 5:
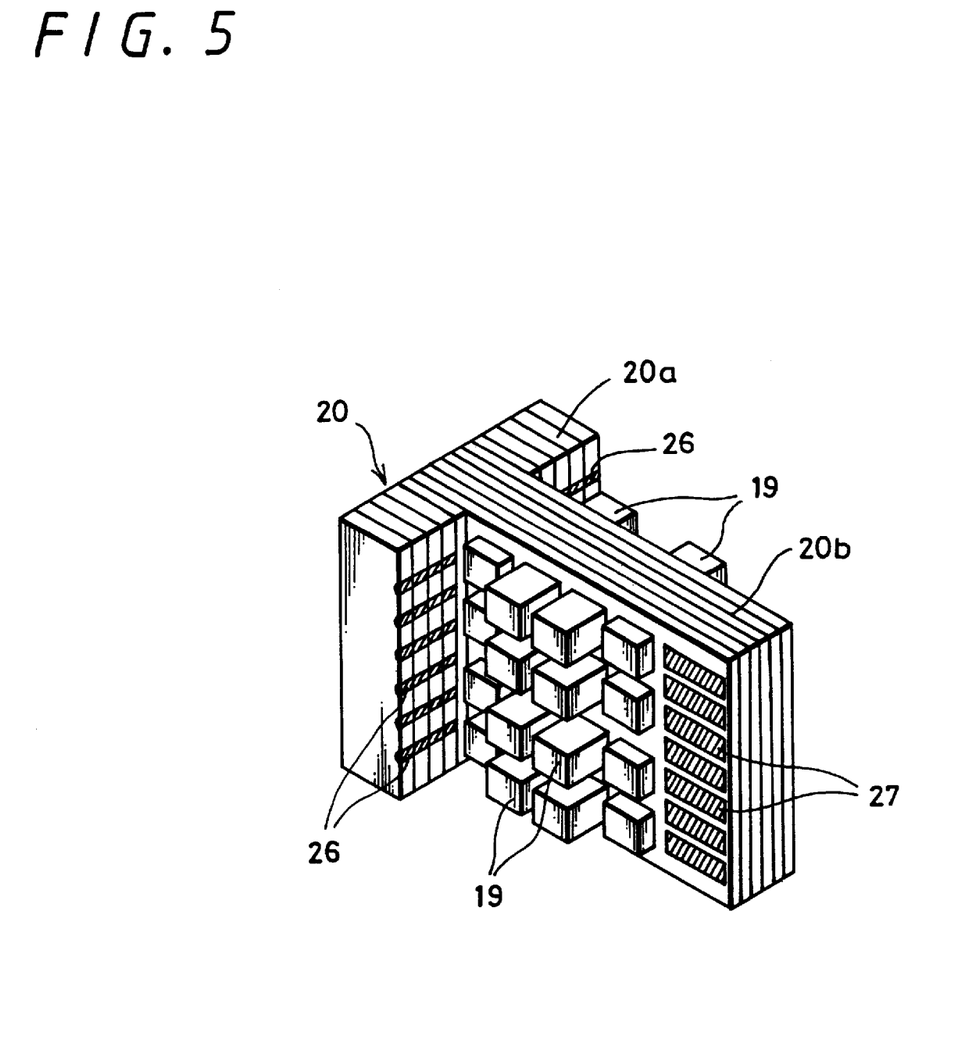

As shown in FIG. 5, the circuit board 20 is constituted by integrally forming the vertical substrate 20a and the horizontal substrate 20b with a multilayer ceramic plate. In this case, a plurality of parallel bonding pads 26 and 26 in an opposing position are formed at the back of the vertical substrate 20a and terminal portions 27 and 27 to which a signal cable to be described later is connected are formed at the both sides of an end of the horizontal substrate 20b. The electronic components 19 mounted on the horizontal substrate 20 are electrically connected with the bonding pad 26 and terminal portion 27 by a land portion exposed to the substrate surface through a not-illustrated internal pattern previously formed on the multilayer ceramic plate.

Figure 6A:
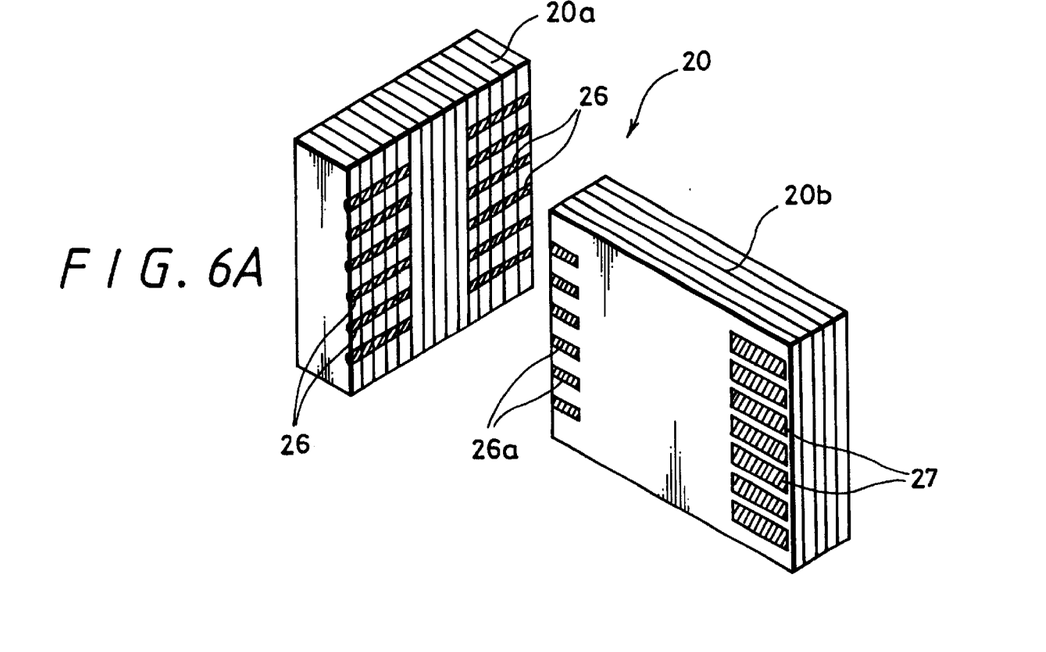
FIG. 6A is a perspective view of a circuit board constituted of two members separated from each other and FIG. 6B is a perspective view of the circuit board constituted of two members combined with each other.
Figure 6B:
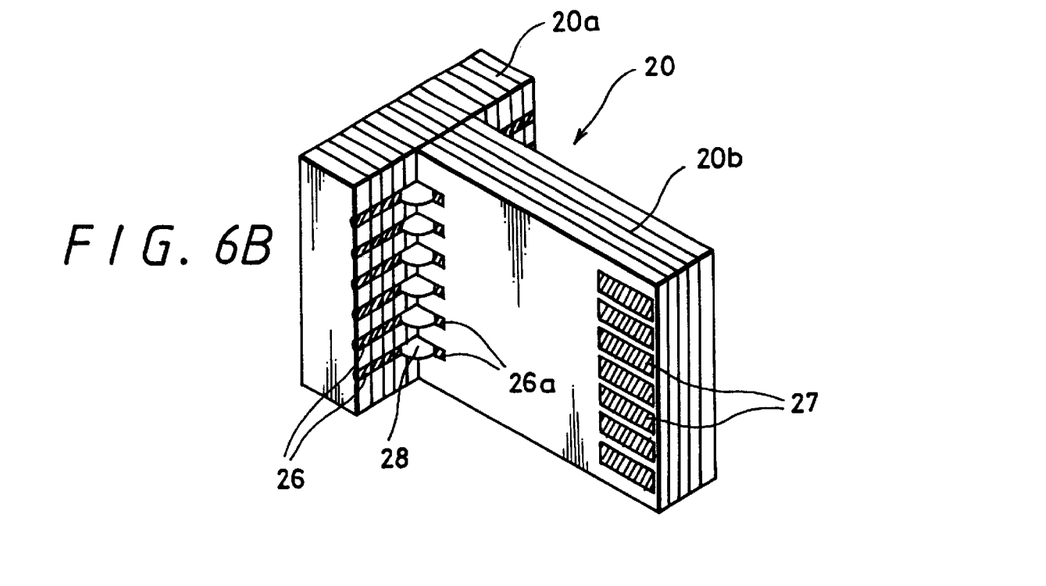

Moreover, as shown in FIG. 6A, the circuit board 20 is permitted to separately form the vertical substrate 20a and the horizontal substrate 20b and then, bonding them each other by an epoxy-based adhesive. In this case, it is possible to improve the bonding strength between the vertical substrate 20a and the horizontal substrate 20b by forming a pad 26a on the horizontal substrate 20b so as to be adjacent to the bonding pad 26 formed on the vertical substrate 20a and bonding the both pads 20a and 20b each other by solder 28.

The solid-state imaging chip 18 is electrically connected with the circuit board 20 by a connection means 29 such as a bonding wire or a pattern-formed film (this example uses a pattern-formed film) and the like. One end of the connection means 29 is connected to the bonding pads 25 and 25 at the front surface of the outer periphery of the solid-state imaging chip 18 and then, bent along the outline plane of the solid-state imaging chip 18 and moreover bent along the back of the vertical substrate 20a of the circuit board 20 and the other end of the connection means 29 is connected to the bonding pads 26 and 26. A pattern on a film is formed through pattern formation in accordance with metallization after polishing the end surface in order to increase the smoothness of the end surface, pattern formation in accordance with pattern printing, or pattern formation in accordance with laser trimming and the like after metallizing the end surface.

A signal cable 30 constituted of a multicore cable is connected to the terminal portions 27 and 27 of the circuit board 20 and the signal cable 30 passes through the soft portion 4 and connects with the operating portion 5.

A cover 31 made of plastic such as polyimide, polyphenylene-sulfide, or epoxy resin or an insulated metal superior in strength and humidity resistance is fitted to the front of the main body portion 14 and a mouthpiece 32 is set to the opening of the body 14 so as to be removable toward the front end. A resin or rubber tube 33 is set to the rear end of the mouthpiece 32 so that a treatment tool such as a forceps and the like can be inserted into or extracted from the mouthpiece 32 through the tube 33 by operating the operating portion 5.

Furthermore, a nozzle tube 34 for cleaning the surface of the object glass at the front surface of the optical lens system 17 is set to the upper portion adjacent to the lens barrel 21. A water feed tube 35 communicating with the operating portion 5 is connected to the nozzle tube 34 so that the surface of the object glass is cleaned by water or air supplied. from the water feed tube 35.

Furthermore, a plurality of wires 36 are combined in the circumferential direction at the rear end of the tip pipe 16 and it is possible to change camera angles by using these wires 36 and thereby remote-controlling the bend portion 3 through the handle operation of the operating portion 5. Moreover, the joint piece 15 and the outer periphery of the tip pipe 16 are protected by a covering tube 38 through a mesh line 37 for preventing radiation and reinforcing them. Furthermore, the joint between the cover 31 and the covering tube 38 is sealed by an adhesive 39 in order to keep airtightness.

Figure 7:
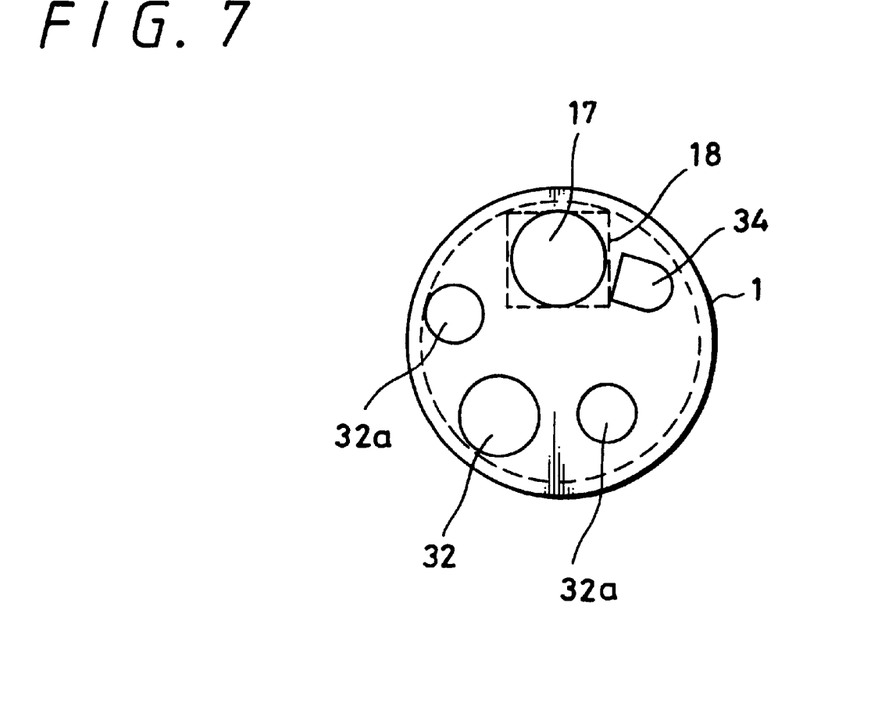
FIG. 7 is a layout drawing of an endoscope comprising a simple-eye camera viewed from the front side.
Figure 8:
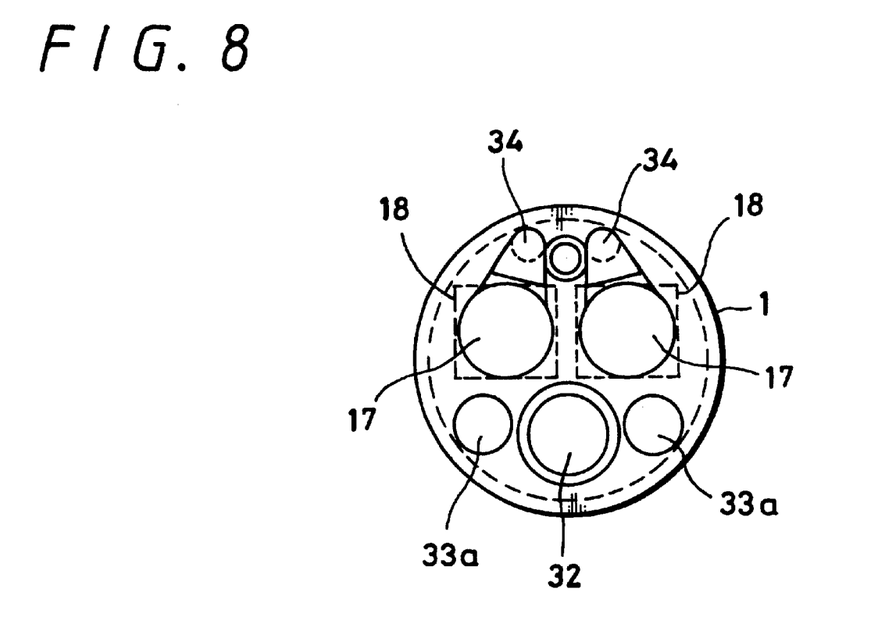
FIG. 8 is a layout drawing of an endoscope comprising a compound-eye camera viewed from the front side.

FIGS. 7 and 8 show arrangements of two types of imaging units when viewing the endoscope 1 from the front side. FIG. 7 shows the endoscope of a simple-eye camera using a set of imaging units. In this case, the optical lens system 17 and the solid-state imaging chip 18 coaxial with the optical axis of the system 17 are arranged at the upper central portion of the endoscope 1. Moreover, a pair of light guides 32a and 32a not illustrated in FIG. 3 is set to the right and left portions of the mouthpiece 32 into or from which a treatment tool such as a forceps is inserted or extracted one each so as to illuminate a portion to be imaged.

FIG. 8 shows a compound-eye camera using two sets of imaging units. In this case, a pair of optical lens systems 17 and a pair of imaging chips 18 coaxial with the optical axis of the systems 17 are present at the left and right and thereby, a portion to be imaged can be three-dimensionally viewed. Moreover, a pair of light guides 33a and 33a is set to the right and left portions of the mouthpiece 32 into or from which a treatment tool such as a forceps and the like is inserted or extracted so as to illuminate a portion to be imaged.

An endoscope of the present invention is constituted as described above and the outside diameter of the front end of the endoscope is determined by the rate (share) occupied by the circuit board 20 mounting the solid-state imaging chip 18 and electronic components 19. That is, in the case of the present invention, the circuit board 20 is set in an area equal to or smaller than the projection area of the not-packaged solid-state imaging chip 18.

More minute description is made below by referring to FIG. 4. The vertical substrate 20a of the circuit board 20 can be set in the projection area of the solid-state imaging chip 18, only the thickness (e.g. 35 to 50 μm) of the connection means 29 such as a bonding wire for connecting the solid-state imaging chip 18 with the circuit board 20 or a pattern-formed film is protruded in the vertical direction of the solid-state imaging chip 18, and thus the size of the substrate 20 is substantially equal to the projection area of the solid-state imaging chip 18.

Moreover, because the electronic components 19 are mounted on the upper and lower faces of the horizontal substrate 20b when a stepped portion is formed to the vertical substrate 20a, it is possible to set the components 19 in the projection area of the solid-state imaging chip 18. Furthermore, because the terminal portion 27 to which the signal cable 30 is connected is also provided at an end of the horizontal substrate 20b where the electronic components 19 are mounted, the solder filling allowance when fixing the signal cable 30 to the terminal portion 27 can be kept in the projection area of solid-state imaging chip 18.

The vertical substrate 20a and horizontal substrate 20b are kept within the side surface of the solid-state imaging chip 18 in the horizontal direction of the solid-state imaging chip 18 and the signal cable 30 is also kept within the side surface of the solid-state imaging chip 18.

Therefore, because an endoscope of the present invention can three-dimensionally accomodate the terminal portion 27 in the projection area of the not-packaged solid-state imaging chip 18 together with the circuit board 20, electronic components 19 mounted on the circuit board 20, and signal cable 30, the endoscope has advantages that it is possible to downsize a solid-state imaging device and thereby, decrease the front end of an endoscope in diameter.

The present invention is not restricted to the above-mentioned and illustrated embodiment. Various modifications of the present invention are permitted as long as the modifications do not deviate from the gist of the present invention.

For this embodiment, a case is described in which the substrate 20b is perpendicularly set to the vertical substrate 20a fixed to the back of the solid-state imaging chip 18 on the circuit board 20. It is also permitted to set the substrate 20b longitudinally to the substrate 20a. In this case, electronic components are mounted on stepped portions formed on right and left surfaces of the substrate 20b to the vertical substrate 20a and moreover, a terminal portion to which the signal cable 30 is connected is also provided at an end of the substrate 20b on the side which electronic components are mounted on.

Moreover, a solid-state imaging device of the present invention can be applied not only to the imaging camera of an endoscope but also to an imaging camera such as a tube-type CCD camera and the like.

As described above, in the case of a solid-state imaging device of the present invention, electronic components and the terminal portion of a signal cable mounted on a circuit board can be set in the projection area of a not-packaged solid-state imaging chip. Therefore, it is possible to three-dimensionally constitute the solid-state imaging device at a high density and downsize an imaging unit. Thereby, in the case of using the solid-state imaging device for an electronic endoscope, an advantage is obtained that the front end of the endoscope can be decreased in diameter.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. A solid-state imaging device comprising:
   a not-packaged solid-state imaging chip;
   a circuit board which is combined with a plane of the solid-state imaging chip opposite to an imaging plane of the solid-state imaging chip and having a vertical substrate fixed to the plane of the solid-state imaging chip and a horizontal substrate orthogonal to the vertical substrate, wherein at least one electronic component is mounted on the circuit board; and
   a connection means including a film on which a wiring pattern is formed, the wiring pattern being for electrically connecting a bonding pad provided for an outer peripheral portion of the imaging plane of the solid-state imaging chip with a bonding pad provided on the vertical substrate of the circuit board, a thickness of said film protrudes substantially 35 to 50 μm in a vertical direction over a top of the imaging chip; wherein said electronic component is mounted on the horizontal substrate of the circuit board formed to be lower than an outline of said solid-state imaging chip and a signal cable is connected to an end of said horizontal substrate so that said electronic component mounted on said circuit board and a terminal portion of the signal cable are arranged in a projection area of said solid-state imaging chip.

2. A solid-state imaging device as claimed in claim 1, wherein said vertical substrate and said horizontal substrate are respectively constituted of a multilayer ceramic substrate.

3. A solid-state imaging device as claimed in claim 1, wherein one end of said connection means is bent along the outline of said solid-state imaging chip and moreover bent along the back of said vertical substrate.

4. A solid-state imaging device as claimed in claim 1, applied to an electronic endoscope using said solid-state imaging chip as an imaging means.

5. An endoscope comprising:
   a solid-state imaging device having:
      a not-packaged solid-state imaging chip;
      a circuit board which is combined with a plane of the solid-state imaging chip opposite to an imaging plane of the solid-state imaging chip and having a vertical substrate fixed to the plane of the solid-state imaging chip and a horizontal substrate orthogonal to the vertical substrate, wherein at least one electronic component is mounted on the circuit board; and
      a connection means including a film on which a wiring pattern is formed, the wiring pattern being for electrically connecting a bonding pad provided for an outer peripheral portion of the imaging plane of the solid-state imaging chip with a bonding pad provided on the vertical substrate of the circuit board, a thickness of said film protrudes substantially 35 to 50 μm in a vertical direction over a top of the imaging chip; wherein said electronic component is mounted on the horizontal substrate of the circuit board formed to be lower than an outline of said solid-state imaging chip and a signal cable is connected to an end of said horizontal substrate so that said electronic component mounted on said circuit board and a terminal portion of the signal cable are arranged in a projection area of said solid-state imaging chip.

* * * * *